US00PP13786P29

(12) United States Plant Patent
Holtkamp, Sr.

(10) Patent No.: US PP13,786 P2
(45) Date of Patent: May 6, 2003

(54) AFRICAN VIOLET PLANT NAMED 'EVERLOVE'

(75) Inventor: Reinhold Holtkamp, Sr., Nashville, TN (US)

(73) Assignee: International Plant Breeding AG, Liebefeld (CH)

( * ) Notice: Subject to any disclaimer, the term of this patent is extended or adjusted under 35 U.S.C. 154(b) by 0 days.

(21) Appl. No.: 10/046,748

(22) Filed: Jan. 17, 2002

(51) Int. Cl.[7] ..... A01H 5/00
(52) U.S. Cl. ..... Plt./270

(58) Field of Search ..... Plt./268, 267, 270

*Primary Examiner*—Kent Bell
(74) *Attorney, Agent, or Firm*—Foley & Lardner

(57) ABSTRACT

A new and distinct cultivar of African Violet named 'Ever-Love' particularly characterized by its multiflorescence trait; single, violet-shaped, bright purplish-red flowers with a wide light pink, wavy edge, ending with a finely-frilled greenish edge; strong, upright flower stems that curve slightly toward the center to form a compact flower bouquet above the leaves; dark green, wavy, heart-shaped leaves; vigorous and extra large growth habit; flowering 12–13 weeks after potting, and long-lasting and non-dropping flowers.

1 Drawing Sheet

LATIN NAME OF THE GENUS AND SPECIES OF THE PLANT CLAIMED

*Saintpaulia ionantha.*

VARIETY DENOMINATION

'Everlove'.

BACKGROUND OF THE INVENTION

The present invention comprises a new and distinct cultivar of African Violet plant, botanically known as *Saintpaulia ionantha*, and hereinafter referred to by the cultivar name 'EverLove'.

The new cultivar was referred to during the breeding and selection process by the designation 'R 28/5' and is a product of a planned breeding program. The new cultivar originated from a cross made by the inventor, Reinhold Holtkamp, Sr., in the controlled breeding program Nashville, Tenn. The female, or seed parent was a cultivar designated 'P 40/9 white muflo Bie' (unpatented). The male, or pollen parent was a cultivar designated 'Q 6/2' (unpatented). 'P 40/9 white muflo Bie' was produced from plants derived from African Violet seeds incubated for 6 years in a weightless environment in space on the Long Duration Exposure Facility.

In comparison to the instant plant, the female parent is a cultivar having white flowers without the light green edge, compact and multiflorescent. The male parent is a cultivar having purple-red flowers with white edges, semi-double, frilled, and non-multiflorescent. The flowers have a less vibrant purplish color than the flowers of 'EverLove', and lacks the light green edge. The leaves of the male parent are medium green and plain whereas the leaves of 'EverLove' are dark green and crenate.

'EverLove' was discovered and selected by the inventor as a flowering plant within the progeny of the stated cross in a controlled environment in Nashville, Tenn. Asexual reproduction of the new cultivar by leaf cuttings, as performed by the inventor in Nashville, Tenn., has demonstrated that the combination of characteristics as herein disclosed for the new cultivar are firmly fixed and retained through successive generations of asexual reproduction. The new cultivar reproduces true-to-type.

'EverLove' has not been observed under all possible environmental conditions. The phenotype may vary significantly with variations in environment such as temperature, light intensity and day length without any change in genotype. The following observations, measurements and values describe the new cultivar as grown in Nashville, Tenn. and Haffen, Germany under greenhouse conditions which closely approximate those generally used in commercial practice.

BRIEF SUMMARY OF THE INVENTION

The following characteristics have been repeatedly observed and are determined to be basic characteristics of 'EverLove', which in combination distinguish this African Violet as a new and distinct cultivar:

1) Multiflorescence characteristic;

2) A single crown as large as 30–40 cm in diameter;

3) Strong, upright flower stems curving slightly toward the center;

4) Single violet-shaped bright purplish-red flowers with wide, wavy light pink edges ending with a finely frilled greenish edge, particularly on the 2 smaller petals;

5) Each plant carries 10–14, and sometimes more, upright flower stems each of which carries 13–18, and sometimes more, flowers;

6) Long-lasting, non-dropping flowers;

7) Vigorous and compact growth;

8) Plant saleable 12–13 weeks after potting;

9) Seed capsules are visible above the petals;

10) Dark green, wavy, heart-shaped leaves; and

11) After maturity the flowers dry off, and remain on the peduncle without becoming infected by Botrytis.

The new cultivar is most similar to 'EverHarmony' (U.S. Plant patent application Ser. No. 10/046,984). Both cultivars have the same parents and display the multiflorescence trait, have the same extra large growth habit and same type leaves and flower shape with the greenish edge. However, 'EverLove' has bright purplish-red flowers with a wide light pink edge and finely frilled greenish edge and dark green leaves whereas 'EverHarmony' has bi-colored white and light pink flowers and medium green leaves.

BRIEF DESCRIPTION OF THE DRAWING

The accompanying color photographic drawing shows a typical plant of the new cultivar 'EverLove'. The colors appearing in the photographic drawing are as true as possible with color illustrations of this type.

The photographic drawing is a top view of 'EverLove' depicting the leaves and flowers.

DETAILED BOTANICAL DESCRIPTION

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn. Measurements were taken 16–18 weeks from potting, as grown in a 6" pot.

Parentage:

*Male parent.*—'Q 6/2'.

*Female parent.*—'P 40/9 white muflo Bie'.

Propagation: Leaf cuttings.

Plant: 11 cm to 14 cm tall when grown in pots, and 30–40 cm in diameter when fully grown.

*Leaves.*—General form: Heart-shaped. Size: 85–95 mm wide and 85–95 mm long. Apex: Emarginate. Margin: Serrate to crenate. Texture: Leatherlike. Aspect: Wavy, hairy, shiny. Veins: Upperside: yellow-green, RHS 147 A and darker; underside: well pronounced, light green, RHS 147 D, shiny. Color (upperside): Yellow-green RHS147 A and a shade closest to but darker than RHS 147 A. Color (underside): Between greyed-purple RHS 187 D and RHS 186 A. Petiole: Strong, light green, RHS 147 C, with touches of grey-purple between RHS 187 A and RHS 183 A on the underside, purplish-brown, between RHS 187 A and RHS 183 A on upper side, hairy.

*Flowers.*—Buds: Bell-shaped, purplish red, RHS 78 B to RHS 78 C, with greenish frilled edge visible, RHS 145 C to RHS 145 D, 8–10 mm in length, and 7–8 mm in width just before opening. Sepals: Five (5), one sepal for each flower petal; spear shaped, 4–6 mm in length, 1.5 to 2 mm in width at the base and 0.5 to 1 mm in width at the tips; margins are entire, color: upperside purplish brown, RHS 200 C, underside purplish brown, RHS 200 C to RHS 200 D. Calyx: Shape: Funnel-shaped. Peduncle: Character: Strong upright, hairy; 20–25 mm in length, 1 mm diameter. Color: purplish brown, RHS 187 A.

*Individual flowers.*—Size: 35–40 mm in width (as measured when pressed flat), 30–35 mm in length (as measured from the top of the small petals to the bottom of the large middle petal). Shape: Single violet-shaped with finely frilled, wavy edge. Petals: 5 (3 large, 2 small); small petals are 12–14 mm in length and 10–13 mm in width; large petals are 18–22 mm in both length and width; margins are wavy and finely frilled; rounded apex shape. Color (upperside): Red-purple RHS 71 A with edges being purple RHS 78 D and lighter, RHS 75 C to RHS 75 D. Fine frilled edge of yellow-green RHS 145 C to RHS 145 D particularly on the 2 smaller petals. Occasionally, the green edge is lacking. Under cooler temperatures and more intensive lighting, the purplish red tends to intensify. Color (underside): Purple RHS 78 B in the center radiating to RHS 78 C and RHS 78 D and lighter, RHS 75 C to RHS 75 D; occasional finely frilled green edge yellow-green RHS 145 C to RHS 145 D. Borne: Each of the flower stem carries 13–18 and more flowers on strong, upright peduncles that are free standing above the leaves, thereby forming a compact bouquet. Flowering habit: Flowers 12–13 weeks after potting. Lastingness of the individual bloom: 4–6 weeks under good growing conditions.

*Reproductive organs.*—Stamens: Two (2); Anthers: 2 composed of 4 anther cells, seed capsules push slightly through. Pistil: 1. Filaments: Yellowish white, 3–4 mm long. Pollen Color: Yellow RHS 7 A, moderate production. Styles: 6–7 mm long, purplish red, base of ovary light green.

*Roots.*—Normally developed, white when young, turning slightly brownish when older.

Disease resistance: 'EverLove' has shown very good resistance to all major violet diseases.

General observations: 'EverLove' is a very attractive cultivar due to its abundance of bright purplish-red flowers with wide, wavy, light pink edges ending with a finely frilled greenish edge, particularly on the 2 smaller petals. Furthermore, it is an outstanding cultivar due to the multiflorescence trait in which the cultivar has 2 to 3 flower stems emerging out ot each leaf internode thereby continuously giving the cultivar new buds before the old flowers have wilted. A nice flower bouquet which is free-standing above the leaves. Under ideal growing conditions, the flowers develop 12–13 weeks after planting on unrooted plantlet. 'EverLove' is never without blooms. Each of the 10–14, or more, strong flower stems carries 13–18, or more, single violet-shaped flowers with wavy, frilled edges. 'EverLove' is an extra large cultivar, designed to be grown in 15 cm pot. The plant also may be successfully grown in a 10 cm pot within a 8–10 week time period from potting to finish. The profuse flower bouquet is surrounded by large, dark-green, heart-shaped, wavy leaves. The flowers are long-lasting and non-dropping and the seed capsules push slightly through.

I claim:

1. A new and distinct African Violet plant named 'EverLove', as described and illustrated herein.

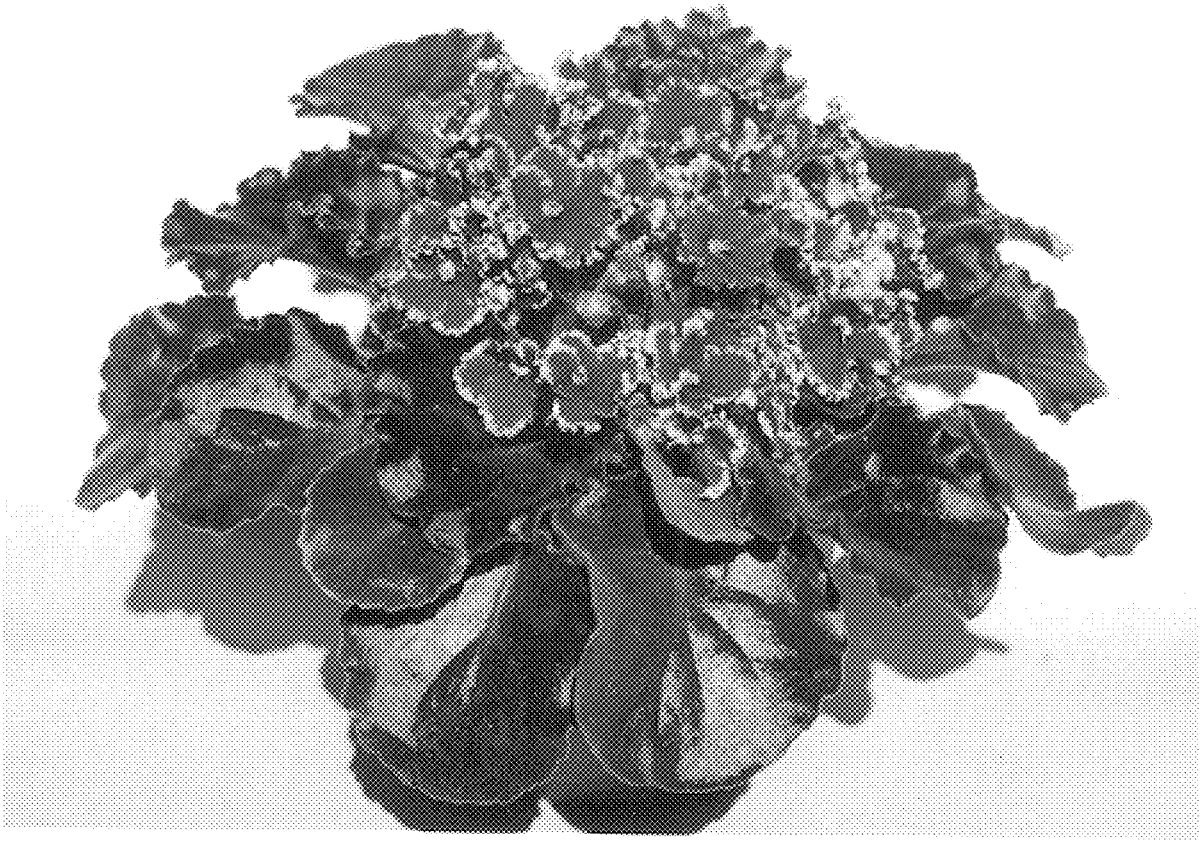

* * * * *